(12) United States Patent
Figueredo et al.

(10) Patent No.: US 11,169,164 B2
(45) Date of Patent: Nov. 9, 2021

(54) SYSTEM FOR BIOLOGICAL SAMPLE COLLECTION, EXAMINATION AND READING IN QUICK BIOCHEMICAL TESTS AND DATA MANAGEMENT

(71) Applicant: HI TECHNOLOGIES S.A., Curitiba (BR)

(72) Inventors: Marcus Vinicius Mazega Figueredo, Curitiba (BR); Sérgio Renato Rogal Junior, Curitiba (BR); Marcelo Júnior Cossetin, Curitiba (BR); Raquel Dos Santos Verissimo, Curitiba (BR); Renan Nepomoceno Pinto, Curitiba (BR); Alisson Ravaglio Santos, Curitiba (BR); Gabriel Herman Bernardim Andrade, Curitiba (BR); Marcelo Emanuel Melani Camati, Curitiba (BR)

(73) Assignee: HI TECHNOLOGIES S.A., Curitiba (BR)

( * ) Notice: Subject to any disclaimer, the term of this patent is extended or adjusted under 35 U.S.C. 154(b) by 88 days.

(21) Appl. No.: 16/607,819

(22) PCT Filed: Apr. 13, 2018

(86) PCT No.: PCT/BR2018/050101
§ 371 (c)(1),
(2) Date: Oct. 24, 2019

(87) PCT Pub. No.: WO2018/195617
PCT Pub. Date: Nov. 1, 2018

(65) Prior Publication Data
US 2020/0182895 A1    Jun. 11, 2020

(30) Foreign Application Priority Data

Apr. 25, 2017 (BR) .................... BR1020170085490

(51) Int. Cl.
*G01N 35/00* (2006.01)
*G16H 10/40* (2018.01)

(52) U.S. Cl.
CPC . *G01N 35/00871* (2013.01); *G01N 35/00732* (2013.01); *G16H 10/40* (2018.01); *G01N 2035/00841* (2013.01)

(58) Field of Classification Search
CPC ....... G01N 35/00732; G01N 35/00871; G01N 2035/00841; G01N 33/487; G16H 10/40; A61B 5/00
See application file for complete search history.

(56) References Cited

U.S. PATENT DOCUMENTS 3,633,922 A    1/1972  Yokota
5,307,263 A *  4/1994  Brown ............. G01N 33/48792
                                                600/301

(Continued)

FOREIGN PATENT DOCUMENTS

CN    104969068    10/2015
DE    102013101888    8/2014
EP    3028242      6/2016

OTHER PUBLICATIONS

International Search Report prepared by the Instituto Nacional da Propriedade Industrial dated Jun. 14, 2018, for International Application No. PCT/BR2018/050101.

(Continued)

*Primary Examiner* — Shogo Sasaki
(74) *Attorney, Agent, or Firm* — Sheridan Ross P.C.

(57) ABSTRACT

The present invention relates to a system used in remote laboratory assays, having cartridge (C) with a reagent strip (TR) a reader (L) with a dedicated hardware (HDL) and a dedicated software (SDL), a local remote hardware (HRL) with a dedicated software (SDHL), an external served hardware (HES) with a data base (BD) and a dedicated software (Continued)

Figure 1:
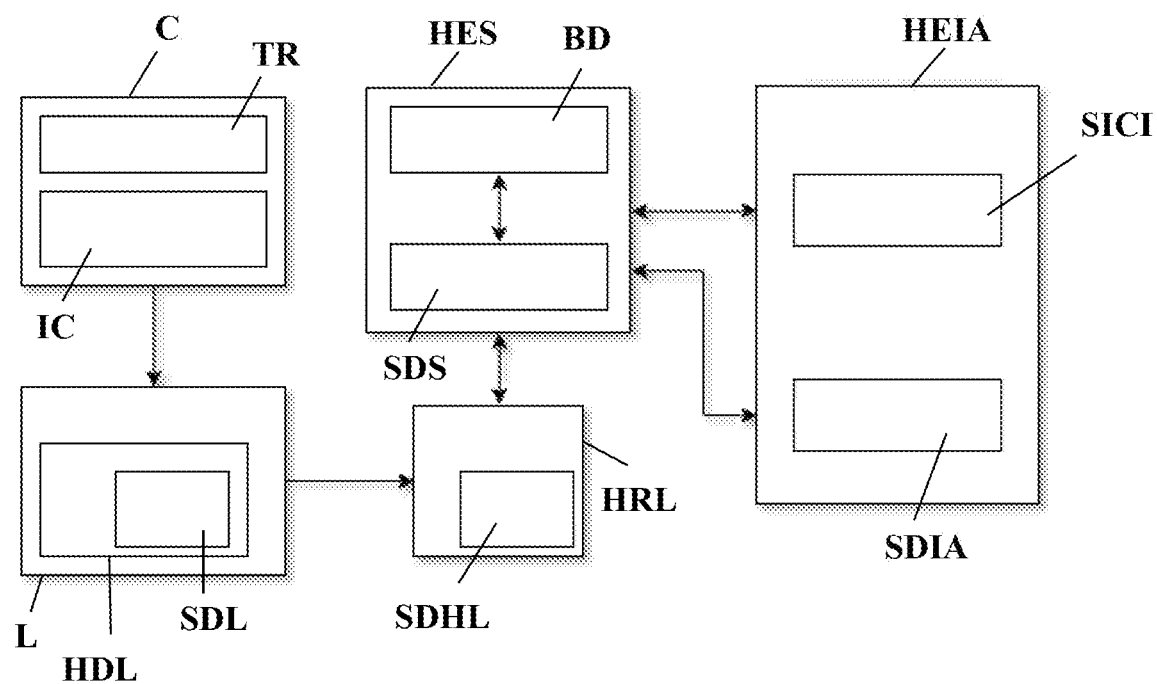

(SDS) and an external hardware with an access interface (HEIA) with an interface software connected to the Internet (SICI) and dedicated software (SDIA), which reads the parameters of the cartridge for collecting various types of biological samples and transmits data, allowing the data to be accessed remotely, with the advantages of being easy to use, of optimizing workflows, of being easy for users to learn, of allowing new exams to be easily and conveniently recorded, of being modular, compact, smaller, portable, ergonomic, user-friendly, intuitive, more practical and less expensive.

4 Claims, 3 Drawing Sheets

(56) References Cited

U.S. PATENT DOCUMENTS

| | | | | |
|---|---|---|---|---|
| 5,899,855 | A | * | 5/1999 | Brown ............. G01N 33/48792 600/301 |
| 6,168,563 | B1 | * | 1/2001 | Brown ............. G01N 33/48792 600/301 |
| 6,295,506 | B1 | | 9/2001 | Heinonen et al. |
| 6,471,131 | B2 | | 10/2002 | Okada et al. |
| 6,494,830 | B1 | * | 12/2002 | Wessel ................ A61B 5/335 600/300 |
| 9,311,520 | B2 | | 4/2016 | Burg et al. |
| 2003/0234299 | A1 | | 12/2003 | Hosoda et al. |
| 2013/0189794 | A1 | | 7/2013 | Emeric et al. |
| 2016/0025639 | A1 | | 1/2016 | Jakubowicz |

OTHER PUBLICATIONS

"Reflotron® Plus Information Booklet," BioStat Diagnostic Healthcare, Apr. 2007, 28 pages [retrieved online from: photos.labwrench.com/equipmentManuals/11023-6349.pdf].

International Search Report prepared by the Instituto Nacional da Propriedade Industrial dated Jun. 8, 2018, for International Application No. PCT/BR2018/050100.

* cited by examiner

SYSTEM FOR BIOLOGICAL SAMPLE COLLECTION, EXAMINATION AND READING IN QUICK BIOCHEMICAL TESTS AND DATA MANAGEMENT

CROSS REFERENCE TO RELATED APPLICATIONS

This application is a national stage application under 35 U.S.C. 371 and claims the benefit of PCT Application No. PCT/BR2018/050101 having an international filing date of 13 Apr. 2018, which designated the United States, which PCT application claimed the benefit of Brazil Patent Application No. BR1020170085590 filed 25 Apr. 2017, the disclosures of each of which are incorporated herein by reference in their entireties.

The present patent relates to a system for collecting, examining and reading biological samples in quick biochemical tests and data management applied in healthcare in general and in Point-Of-Care Testing (POCT) in particular, for the purpose of clinical diagnosis with reduction of the time of release of results and allowing low volume of cartridge-collected biological sample and aiming to provide a quick response that can lead to confirmation or follow-up of a disease through optimized design with mechanics, electronics and dedicated software that reads various types of biological samples, like urine, blood, saliva, mucus, feces and others, bringing advantages of ease of use and optimization of operational flows, easy user training, easy and convenient new test registration, being modular, compact, small in size, portable, lightweight, ergonomic, humanized, intuitive, more practical and cost effective.

As is well known by the technical means linked to the manufacture and use of Point-of-Care Testing (POCT) devices, which analyze reagent cartridges for the detection of infectious, viral, chronic, metabolic disorders, among other biological variables, the following reader devices currently exist:

1. Scanadu Scout, a device capable of reading vital signs such as oximetry, temperature, pressure and pulse. Scanaflow, capable of performing a complete urinalysis test using only a "pee stick" and the application of a camera smartphone. Features: Bluetooth® connectivity for smartphone connection; Uses smartphone for storage, processing and display information obtained from performed exams; Reading of vital signs such as temperature, oximetry, respiratory rate, pulse, blood pressure and stress levels; Sensors for Peripheral Oxygen Saturation (SPO2), infrared thermometer and Electrocardiogram (ECG); Application software (app) with exams history, trends and guide for performing of exams; User registration; Twelve reagents including glucose, leukocytes, nitrite, blood in urine, bilirubin, urobilinogen, microalbumin, creatinine, ketone, specific gravity and its pH levels; and Smartphone application that reads the "pee stick", stores and displays the information.

2. Cube Header Diagnostic System, a test reading system capable of assessing and quantifying lateral flow immunochromatographic assays results based on change of color or appearance of bands. Features: Contains only one button for operation; It has 14 segment LCD display for viewing results; Battery power; Storage capacity of 100 results; and measurement time within approximately 3 seconds.

3. Accu-Chek is a device for measuring and controlling blood glucose levels. Features: Ability to read strips reactive to blood glucose level; Memory capable of storing up to 1000 daily records; Programmable reminders for events, alarm clock and date; Power source: three alkaline or lithium batteries; Color display; Automatic activation that activates and deactivates the device when an exam strip is inserted; The device also turns itself off after downtime; Connectivity: Infrared (IR) data input compatible with proprietary software; Bluetooth® for insulin pump connection; Customizable parameters: Language selection, beep and vibration, bolus calculator, display backlight setting, time format selection, carbohydrate unit selection.

4. Cobas H 232 is a Point-of-Care system for detecting cardiac troponin T, CK-MB, myoglobin and NT-proBNP levels, the levels of these blood substances indicate whether the patient has had an acute myocardial infarction or other cardiac problems recently. Characteristics: Readability of cardiac T troponin, CK-MB, myoglobin, D-dimer and NT-proBNP reagent strips; Memory capable of storing up to 500 test records; Power: AC Power supply; Sample Type: Heparinized whole venous blood; Automatic shutdown programmable between 1 and 60 minutes; and measurement position: Operate the meter on a level and vibration-free surface when applying the sample until the required amount has been fully absorbed by the strip.

5. Urisys 1100 is an urine test strip analyzer. Features: Urine Test Strip Analyzer; Wavelengths: 565 nm and 610 nm; Transfer Rate: 100/h; Memory: 100 results; Interface: 2 line, 24 character LCD screen; Built-in thermal printer; Supported Tests: Density, pH, Leukocytes, Nitrite, Protein, Glucose, Urobilinogen, Bilirubin, Hemoglobin. System Interfaces: Serial computer interface, 5-pin DIN socket for keyboard and barcode reader.

6. Coaguchek XS is intended to measure blood clotting time. Features: TP/INR test strip analyzer; TP time amperometric detection system after activation of coagulation with recombinant human thromboplastin; Handling should be done on level surface and without vibration, keeping the monitor in horizontal position; Memory: 100 test results; Interface: Infrared; Power: Four batteries; Number of tests per battery pack: Up to 300 tests or 2 years in standby; Heparin Sensitivity: No, up to 0.8 l.U/ml for UFH and 2 antiXa for LMWH; Integrated QC: In each strip, through the same channel through which the blood passes.

7. Accutrend Plus is a test strip reader capable of performing glucose, cholesterol, triglyceride and lactate tests. Features: glucose, cholesterol, triglyceride and lactate strips analyzer; Measurement ranges: Glucose 20-600 mg/dl (1.1-33.3 mmol/l), cholesterol 150-300 mg/dl (3.88-7.76 mmol/l), triglycerides 70-600 mg/dl (0.80-6.86 mmol/l)), lactate 0.8-21.7 mmol/l (whole blood)—0.7-26 mmol/l (plasma); Sample material a drop of capillary blood; Memory: 100 results; Test principle: Reflectance photometry; and Power: 4 batteries.

8. LABMAXUR0120 from Medmax; Features: Test Speed: 120 strips/hour; Memory: 2000 results; Ability to analyze strips of glucose, bilirubin, ketone bodies, density, pH, blood, protein, urobilinogen, nitrite, leukocytes and vitamins C; LCD display; and Interface: RS232 serial port.

9. Afinion AS100 Analyzer is a multi-assay, fast, cartridge analyzer and can be used with various sample types. This device uses Alere Afinion Tests cartridges, which feature exam information code and sample capillary collection system. Features: Performs HbA1c, Lipid Panel, ACR and CRP tests; Color LCD display; USB connection for code reading and exam printing; connectivity compatible with POCT1-A QC and operator lockout.

10. Alere Prima Analyzer is an assay device for the purpose of counting T cells in a patient's blood. This count helps in the diagnosis and monitoring of patients suffering from immunosuppression caused by the HIV virus. Features: Guarantees the counting result in just 20 minutes; Power: batteries or AC power source; Data file incorporated into the software; Cartridges contain built-in control; Resources: Possibility of immediate implementation of clinical decisions; possibility of operation at the treatment site or in the laboratory; and exam data management (storing, retrieving, printing, reviewing and exporting) and no need for external control of materials.

Searching the Brazilian and foreign patent database, we found the following disclosures:

European Patent EP3028242 "Methods and Systems for Acquiring Diagnostic Information". Methods are described to enable a patient to conveniently test a biological parameter remote from a clinic setting (e.g., at home or work) which provides a way to reduce stress associated with the process. The devices and methods are also adaptable to provide resulting information via a communication network to a remote location and/or a third party (health care provider, health buddy, etc.).

U.S. Pat. No. 6,295,506 "Measurement Apparatus" which discloses a system for measuring the blood glucose level in a sample of a patient's blood. Consumable test strips are provided together with a code which identifies the manufacturing batch of the strip. A measurement unit is provided and is coupled to a mobile telephone. The measurement unit is arranged to receive a test strip and to determine a color change in a reagent due to reaction of the reagent with a blood sample. The identification code is read at the same time by the measurement unit and is transmitted by the mobile telephone to a central database provided by the test strip manufacturer. The database contains identification codes together with associated calibration data. Upon receipt of an identification code, the remote database transmits the associated calibration data to the mobile telephone which uses the calibration data to calculate a test result from the measured change in color. The result can be displayed to the patient on a display of the telephone.

"SYSTEM FOR BIOLOGICAL SAMPLE COLLECTION, EXAMINATION AND READING IN QUICK BIOCHEMICAL TESTS AND DATA MANAGEMENT", object of the present patent, has been developed to overcome the drawbacks, limitations and disadvantages of current systems by means of electronic code identifier with examination data in the collection cartridge, reader with electronics with sensor and processor pre-recorded with dedicated software that reads parameters from the exam data provided by the collection cartridge and various types of biological samples like urine, blood, saliva, mucus, feces and others and transmits data to local hardware and software that manages the data and transmits it to external hardware and software so that it can be accessed remotely by the user, bringing advantages of ease of use and operational flow optimization, easy user training, easy and convenient new exam registration, being modular, compact, small in size, portable, lightweight, ergonomic, humanized, intuitive, more practical and cost effective.

As in previous inventions, in this patent examination results obtained by the reading module are also stored on a data server and can be remotely accessed. This feature allows for better data management and control. An interface is made available to the user, which can be accessed from a mobile phone, computer, notebook, or the like, where it is possible to view the trend of any measurements and also to monitor the exams of interest.

The innovative point of this patent is the ability to work with any type of exam that produces results based on color variation. In addition, the code identifier (IC), QR Code-type or similar, from the cartridge (C) stores all the basic parameters to perform the exam, such as name, reaction time, limits, calibration points, among others. Thus, to enable the system to perform a new exam type, it is only necessary to include the protocol information in the cartridge code.

Another innovative point of this patent is that data, such as serial number, lot and expiration date, for cartridges containing reagent strips (TR) are stored on the server. This makes diagnostics safer and more reliable as it prevents counterfeit cartridges from being used and marketed. Every cartridge has an identification that is provided to the reader and is saved along with the exam result. Thus, it is possible to know the origin and if the cartridge data is true, since its data must be in the system.

Additionally, the system of the present patent has the following characteristics:

1. Automatic identification of exam type: The user does not need to inform what type of exam will be taken. The cartridge has information to perform the exam. This feature also eliminates human error by reporting an incorrect exam;

2. Cartridge reading module is controlled by remote hardware and software: this allows cost reduction as it can control multiple readers at the same time.

3. The user can consult the history of the exams performed and check their evolution;

4. In minutes the results of the exams are obtained; and

5. It has WIFI and Bluetooth® connection.

Current systems present the following technical problems that the present invention solved as follows:

1. Due to the wide variety of types of biological samples, errors can occur in the identification of the exam, solved by the present patent through the automatic exam type identification system: the user does not need to inform which type of exam will be performed, because the Code identifier (QR Code or similar) on the cartridge allows the reader to identify the type of exam;

2. Difficulty in registering new exams, making the operation difficult and time consuming, solved by the present invention by storing the protocol to perform the respective examination in the cartridge, which is provided to the reader;

3. Difficulty in evaluating and interpreting performed measurements, solved by the present invention with the construction of a user-friendly interface that presents trends and statistical data of its measurements;

4. Use of counterfeit cartridges, solved by the present invention with the registration of the cartridges in the database; and 5. Due to the diversity of reagent strips, specialized reading and interpreting devices are used, solved by the present invention with the standardization of the reagent strips and cartridges, thus a single device is capable of reading different types of exams.

In order to obtain the technology of the present invention, incessant research and development was carried out following the following sequence:

Initially the company has always looked for solutions to facilitate and humanize health monitoring of sick people in a hospital setting. Although this approach reaches the people who need care the most, it represents a small portion of the people the company wants to reach. Due to this, some options were studied and considered to serve a larger part of the population as well as to facilitate health care.

Blood tests are widely performed by much of the population and provide important health information, thus enabling preventative measures to be taken to prevent serious events from being triggered. However, the process for taking the exams is bureaucratic.

You first need to feel bad enough to go to the doctor, who will prescribe a battery of tests.

Then go to a laboratory to collect the biological material that will be submitted for analysis. Having the results in hand, the patient should return to the doctor, who will prescribe medication to treat the disease.

Since some methods used in laboratories can be used by the public, the idea has emerged of creating a product that can make testing as simple as measuring pressure or weight in the comfort of home.

Point-of-Care Tests (POCT) are easy to perform and require no laboratory structure. Pregnancy, menopause, and fertility tests can be found at drugstores, but there are yet another multitude of tests such as vitamin D, Sexually Transmitted diseases (STDs), drugs, and viruses.

The invention seeks to take advantage of commercially available tests and to facilitate their use. For this, the present product offers several types of cartridge-encapsulated quick exams and a reader for the interpretation of the exam result through the colorimetric principle. These features allow an untrained lay person to perform the exam of his or her choice with the same confidence as the one performed in the laboratory.

Figure 2:
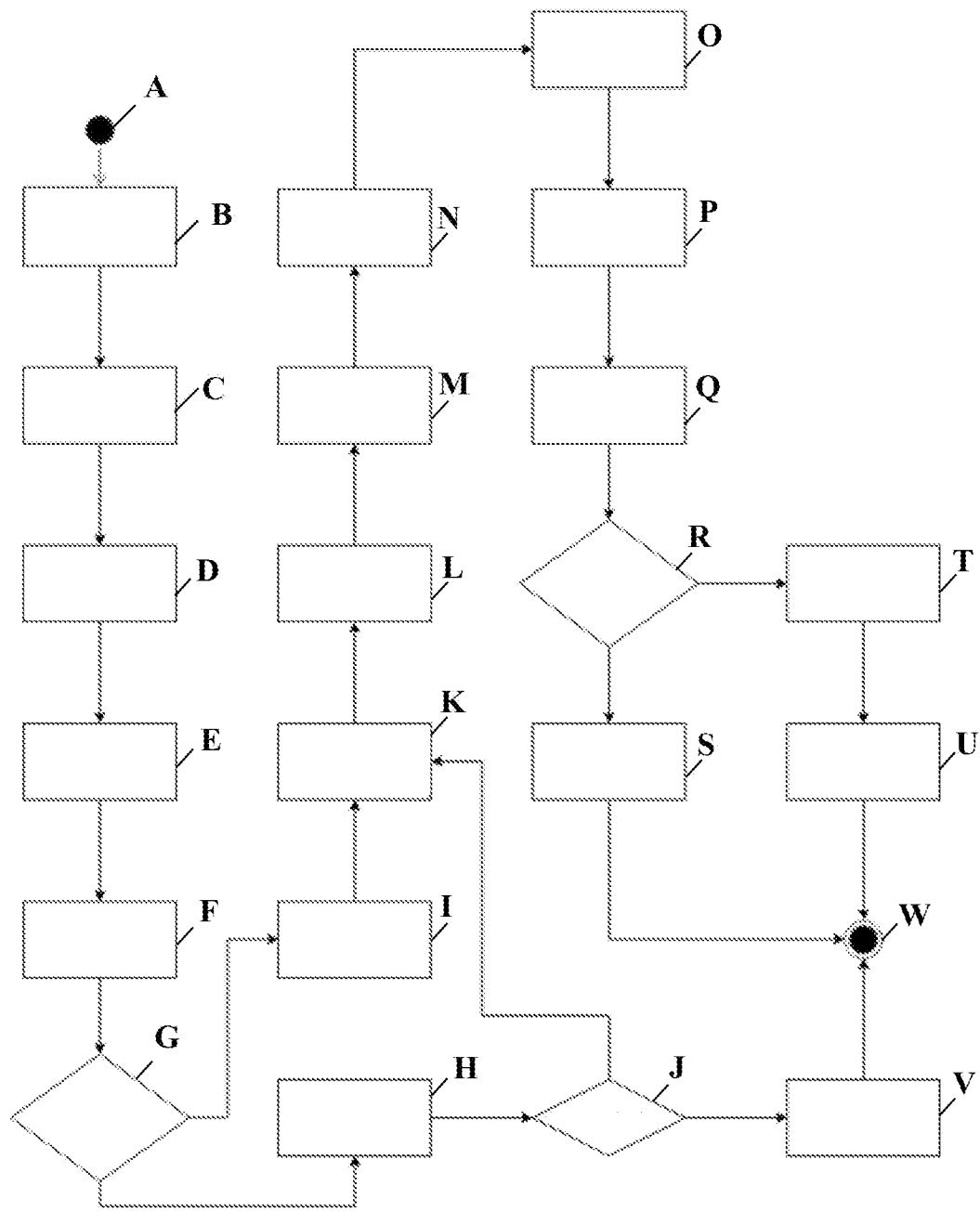
Figure 3:
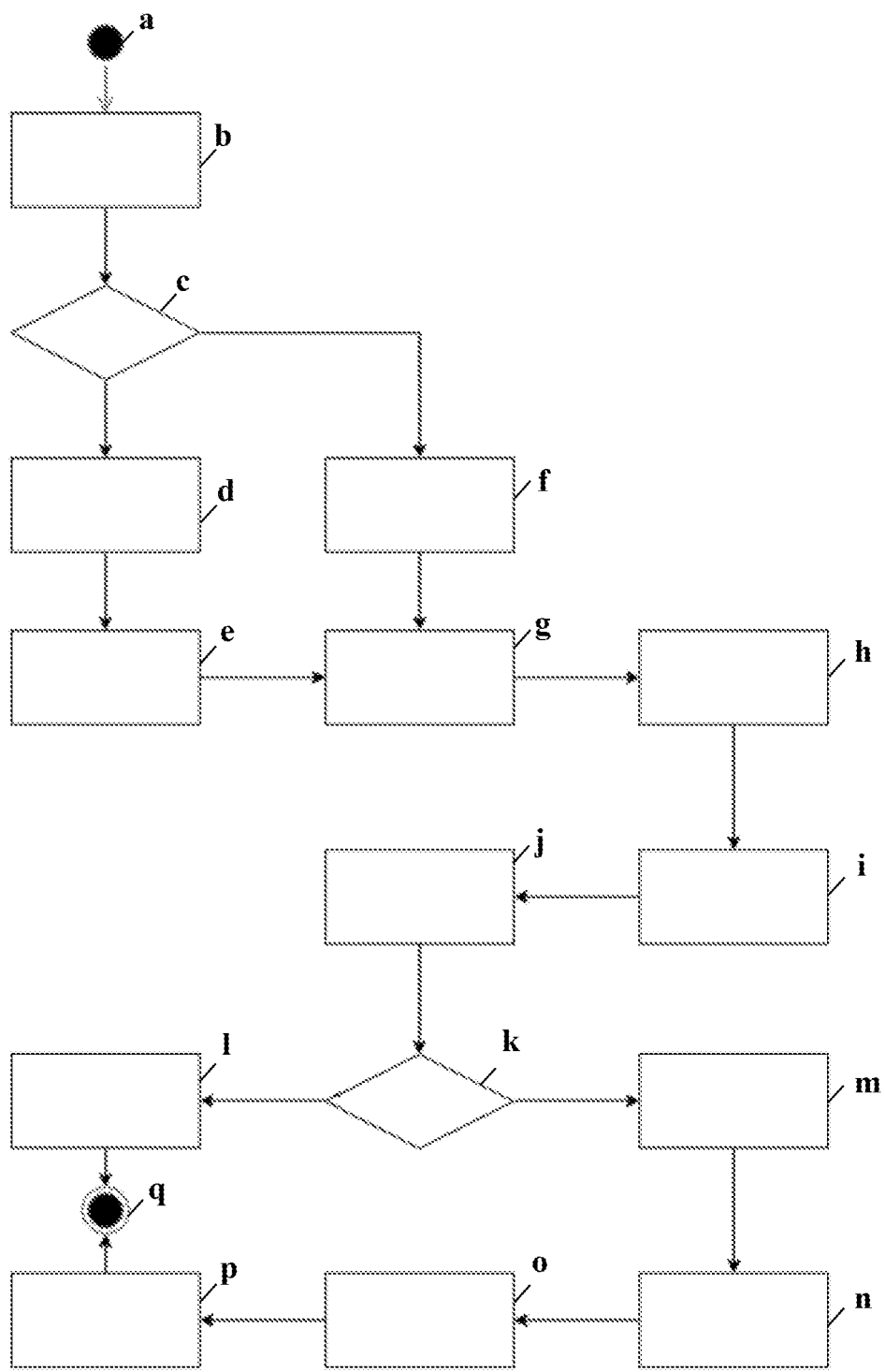

For a better understanding of this patent the following figures are attached:

FIG. 1. showing the block diagram of interconnections between the components of the system from the present patent;

FIG. 2. showing the block diagram of the performed process, including those executed by the dedicated software of the system from the present patent; and FIG. 3. showing the block diagram of the operation of the system from the present patent.

The system of the present invention is comprised of a cartridge assembly (C) having a reagent strip (TR) which produces color-based result, with code identifier (IC) which stores all basic parameters for performing the examination, and which enables the system to perform a new exam type by only including the protocol information in the code identifier (IC) and unidirectionally connected to the reader (L); with reader (L) endowed with dedicated hardware (HDL) and dedicated software (SDL) that transmits the test result data to the local remote hardware (HRL) from the reading of the information and interpreting of the cartridge (C) results together with the sample data and cartridge code and unidirectionally connected to the local remote hardware (HRL) and to the cartridge (C); local remote hardware (HRL), such as a tablet or mobile phone, with dedicated software (SDHL) that receives the exams data and transmits it to the external server hardware (HES) or makes available on the screen the exam result, the data from the sample and cartridge code and patient data and bi-directionally connected to external server hardware (HES) and unilaterally to reader (L); external server hardware (HES) with application server with minimum features of: Gigabit network interface, 1.2 GHz processor, 4 GBytes RAM, storage with 512 GBytes memory, and with database (BD) and dedicated software (SDS) that receives the test result, sample data and cartridge code and patient data and stores it in the database (BD) and is bi-directionally connected to external access interface hardware (HEIA) and to the local remote hardware (HRL); and external hardware with access interface (HEIA), such as mobile phone, tablet or computer with minimum features of: 700 MHz processor, 512MBytes RAM, 512 MBytes of storage memory and endowed with internet connection software (SICI) of Wi-Fi type and dedicated software (SDIA) which makes possible for the user to consult the test result, sample data and cartridge code and patient data and bidirectionally connected to external server hardware (HES).

The process performed including the dedicated software of this system is as follows:
A. START;
B. Adapt the desired sample cartridge;
C. Place the sample in the region indicated on the cartridge;
D. Insert cartridge into desired reader slot;
E. Cartridge code identifier is read and interpreted by the reader;
F. Reader sends exam information to local remote hardware;
G. Does local remote hardware have connection to external server hardware? If yes go to I, if not, go to H;
H. Schedule cartridge validation for connection and go to J;
I. Validates cartridge information;
J. Is cartridge valid? If yes go to K, if not go to V;
K. Starts the exam;
L. Identifies the patient on local remote hardware;
M. Waits for time to finish the exam;
N. Reader captures chemical variations on cartridge test strip;
O. Reader interprets cartridge result and sends to local remote hardware;
P. Local remote hardware assigns test result to patient;
Q. Local remote hardware displays the result and saves it to the local database;
R. Does local remote hardware have server connection? If yes go to T, if not go to S;
S. Local remote hardware schedules exam submission to server and goes to W;
T. Local remote hardware sends scan result to external server hardware;
U. Does exam result available for external access and go to W;
V. Shows the user that the cartridge is not valid; and
W. END.

The operation of the system of the present invention is as follows:
a. START;
b. Connect reader and local remote hardware;
c. Is it the first use? If yes go to d, but go to f;
d. Register establishment in the software of the local remote hardware;
e. Activate Bluetooth®;
f. Enter username and password in the software of the local remote hardware;
g. Connect local remote hardware to the desired reader;
h. Place the biological sample in the cartridge for the chosen examination;
i. Insert the cartridge into the reader;
j. Local remote hardware software displays exam data;
k. Is the cartridge valid for exam? If yes go to m, if not go to l;
l. local remote hardware reports invalid cartridge and go to q;
m. Reader LEDs flash, press the cartridge all the way down;
n. Identify patient data in local remote hardware software;
O. Await for finalization of the exam;
P. Software on local remote hardware displays scan result; and
q. THE END.

What is claimed is:

1. A system for biological sample collection, examination and reading in biochemical tests and data management, comprising a cartridge (C) equipped with a reagent strip (TR) that reproduces results based on color variation, with a code identifier (IC) which stores all parameters for performing the examination and which enables the system to perform a new exam by only including protocol information in the code identifier (IC) and unidirectionally connected to a reader (L); with the reader (L) that transmits test result data comprising a test result to local remote hardware (HRL) from reading information and interpreting results of the cartridge (C) together with sample data and the code identifier (IC) and unidirectionally connected to the local remote hardware (HRL) and to the cartridge (C); the local remote hardware (HRL), comprising dedicated software (SDHL) that receives the test result data and transmits the test result data to external server hardware (HES) or makes available on a screen the test result data, the test result, the sample data, the code identifier (IC), and patient data and bi-directionally connected to the external server hardware (HES) and unilaterally to the reader (L); the external server hardware (HES) comprising an application server with minimum features of: a Gigabit network interface, 1.2 GHz processor, 4 GBytes RAM, storage with 512 GBytes memory, and with a database (BD) and dedicated software (SDS) that receives and stores the test result data, the test result, the sample data, and code identifier (IC), and the patient data in the database (BD) and is bi-directionally connected to external access interface hardware (HEIA) and to the local remote hardware (HRL); and the external access interface hardware (HEIA), comprising minimum features of: a 700 MHz processor, 512 MBytes RAM, 512 MBytes of storage memory and endowed with Internet connection software (SICI) of Wi-Fi type and dedicated software (SDIA) which makes possible for a user to consult the test result data, the test results, the sample data, the code identifier, and the patient data and bidirectionally connected to the external server hardware (HES).

2. The system for biological sample collection, examination and reading in biochemical tests and data management according to claim 1, wherein all the parameters for performing the examination comprise: a name, reaction time, limits, and calibration points to enable the system to perform the new exam.

3. The system for biological sample collection, examination and reading in biochemical tests and data management according to claim 1, wherein the test result data comprises: a serial number, lot and expiration date for the cartridge containing the reagent strip being stored on the external server hardware and saved together with the test result, allowing to know an origin and if cartridge data are true, since the test result data must be in the system.

4. The system for biological sample collection, examination and reading in biochemical tests and data management according to claim 1, wherein the new exam is performed in the following sequence:
   A. START;
   B. Adapt the cartridge from desired sample cartridges;
   C. Place a sample in a region indicated on the cartridge;
   D. Insert the cartridge with the sample into a desired reader slot of the reader, wherein the following complementary sequence is performed:
   E. Read and interpret the code identifier by the reader;
   F. Send, by the reader exam information associated with the cartridge to the local remote hardware;
   G. Does the local remote hardware have a connection to the external server hardware? If yes go to I, if not, go to H;
   H. Schedule cartridge validation for connection and go to J;
   I. Validate cartridge information associated with the cartridge;
   J. Is the cartridge valid? If yes go to K, if not go to V;
   K. Start the new exam;
   L. Identify a patient on the local remote hardware;
   M. Wait for time to finish the new exam;
   N. Capture, by the reader, chemical variations on the reagent strip;
   O. Interpret, by the reader, the test result and sends to the local remote hardware;
   P. Assign, by the local remote hardware, the test result to the patient;
   Q. Display, by the local remote hardware, the test result and saves the test result to the local database;
   R. Does the local remote hardware have a server connection to the external server hardware? If yes go to T, if not go to S;
   S. Schedule, by the local remote hardware, an exam submission to the external server hardware and go to W;
   T. Send, by the local remote hardware, a scan result to the external server hardware;
   U. Test result is available for external access and go to W;
   V. Show the user that the cartridge is not valid; and
   W. END.

* * * * *